United States Patent [19]

Murphy, Jr. et al.

[11] Patent Number: 5,009,503
[45] Date of Patent: *Apr. 23, 1991

[54] AUTOMATED CAPILLARY SCANNING SYSTEM

[75] Inventors: Martin J. Murphy, Jr., Dayton; Jack B. Stubbs, Waynesville; Thomas A. Leonard, Dayton, all of Ohio

[73] Assignee: Hipple Cancer Research Corporation, Dayton, Ohio

[ * ] Notice: The portion of the term of this patent subsequent to Feb. 20, 2007 has been disclaimed.

[21] Appl. No.: 479,959

[22] Filed: Feb. 14, 1990

Related U.S. Application Data

[63] Continuation of Ser. No. 205,725, Jun. 13, 1988, Pat. No. 4,902,132.

[51] Int. Cl.$^5$ .................... G01N 21/51; C12M 1/34
[52] U.S. Cl. .................... 356/339; 356/244; 435/291; 435/296
[58] Field of Search ............... 356/445, 244, 336, 338, 356/339

[56] References Cited

U.S. PATENT DOCUMENTS 3,574,063  4/1971  Bowman ................... 435/291 X
4,616,927  10/1986  Phillips et al. ................ 356/338

OTHER PUBLICATIONS

Bowman, R. L. & Blume, P., Paper Presented at Conference on Engineering in Medicine & Biology, San Francisco, CA, 1966.
Bowman, R. L., Blume, P. & Vurek, G. G., Capillary-Tube Scanners for Mechanized Microbiology, 1967, Science, 158:78–83.
Ulmer, A. J. & Maurer, H. R., The Formation of B-Lymphocyte Colonies in Agar Contained in Glass Capillaries, 1978, Immunology, 34:919–925.
Maurer, H. R. & Henry, R., Drug Evaluation on Haemopoietic Cells in Vitro, 1978, Arzneimittel-Forschung, 28:601–605.
Ulmer, A. J. & Flad, H. D., One-State Stimulation of Human T-Lymphocyte Colony-Forming Units (TL-CFU) in a Micro Agar Culture in Glass Capillaries, 1979, Immunology, 38:393–399.
Ulmer, A. J., Flad, H. D. & Opitz, H. G., T-Lymphocyte Colony Formation of Murine Spleen Cells in a One-Stage Micro Agar Culture, 1981, Journal of Immunological Methods, 40:27–38.
VonHoff, D. D., Forseth, B. J., Huong, M., Buchok, J. B. & Lathan, B., Improved Plating Efficiencies for Human Tumors Cloned in Capillary Tubes Versus Petri Dishes, 1986, Cancer Research, 46:4012–4017.
Matthiessen, H. P., Echarti, C., Gerber, J. & Maurer, H. R., T-Lymphocyte Colony Formation of Murine Thymocytes in Agar Contained in Glass Capillaries, 1987, Blut, 55:517–522.
OMNICON Image Analysis Systems, Promotional Literature, Bausch & Lomb Cellscan: An Automated Capillary Cloning System Scanner.

*Primary Examiner*—Vincent P. McGraw
*Attorney, Agent, or Firm*—Jacox & Meckstroth

[57] ABSTRACT

A plurality of parallel spaced cylindrical capillary tubes contain single cells and/or cell colonies in a medium and gel-like agarose, and the tubes are carried by a frame-like holder supported by a motor driven X-Y translation stage of an automated microscope. The microscope also incorporates an electronic optical detector and an object lens located under the tube holder. The entire contents of each tube are internally illuminated by a precision light beam emitted from a helium-neon laser and reflected by a set of precisely positioned mirrors so that the beam extends axially through each tube when the tube extends across the vertical axis of the object lens. The contents of the tubes are sequentially scanned under the control of special softward within a personal computer, and the intensity of the light reflected outwardly from each cell or cell colony is sensed by the detector and recorded in the computer along with the axial location of the reflecting cell or cell colony. Preferably, the laser light is pure red, the optical detector is sensitive to the red light, and the object lens is focused on the wall of the tube to maximize the signal-to-noise ratio and to obtain full field detection across each tube.

23 Claims, 2 Drawing Sheets

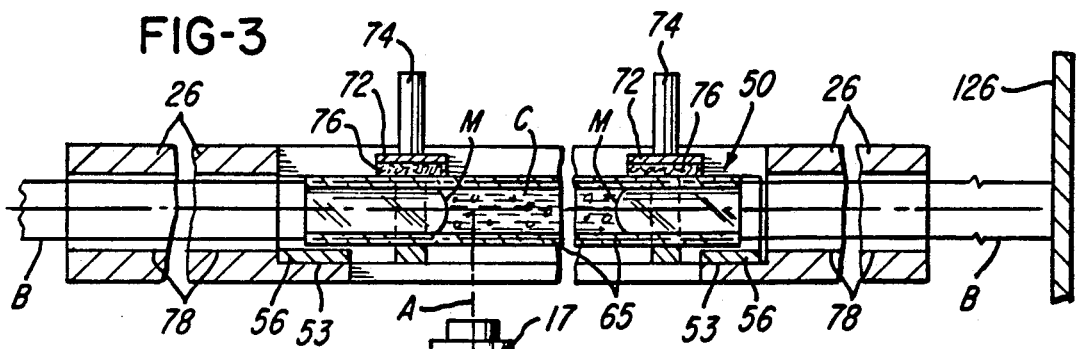
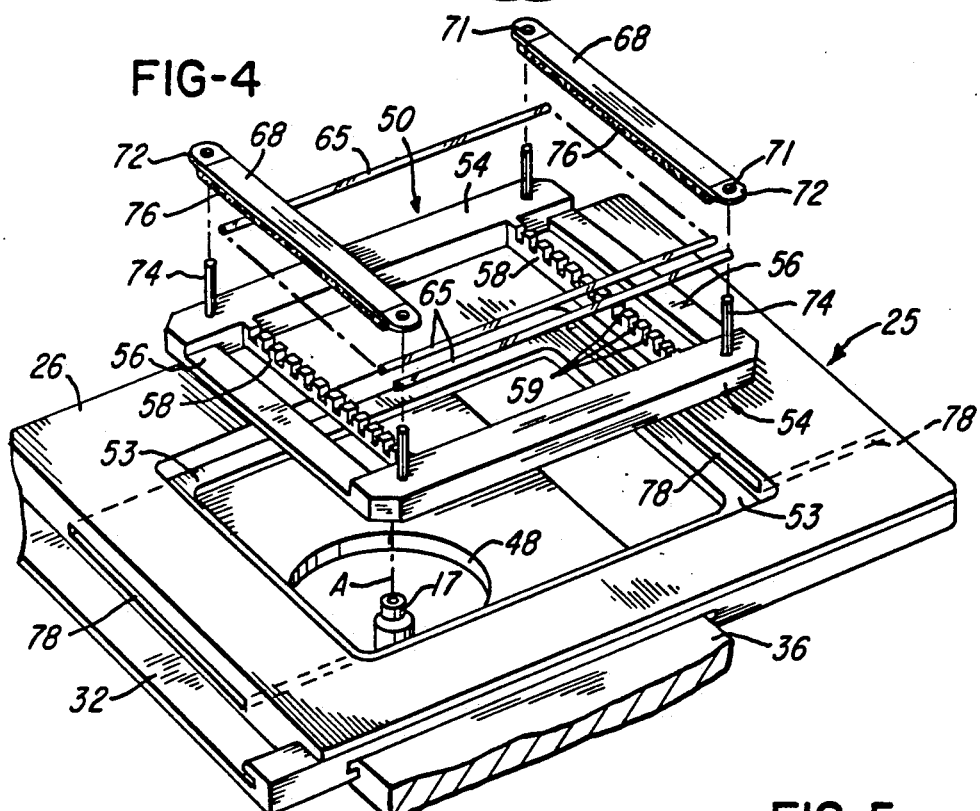
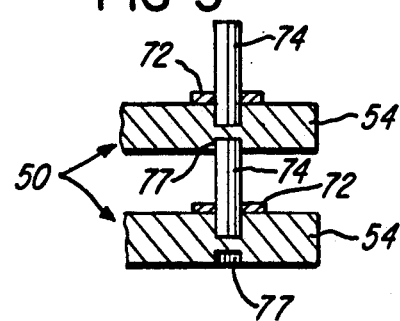

AUTOMATED CAPILLARY SCANNING SYSTEM

This is a continuation of application Ser. No. 205,725, filed June 13, 1988, now U.S. Pat. No. 4,902,132.

BACKGROUND OF THE INVENTION

In the field of biomedical research studies involving the cloning of cells for the purpose of determining the response of human tumor cell colonies to chemotherapeutic drugs, the colonies of tumor cells are commonly grown in a medium and gel-like agarose placed in petri dishes. The cell colonies are exposed to different drugs in various concentrations, and usually, the cell colonies are manually counted by technicians viewing the colonies through a low-powered inverted microscope.

As an alternative to this manual counting procedure which is fatiguing, time consuming, prone to inaccuracies and expensive, an image analyzer has been developed by Bausch & Lomb and has been marketed under the trademark OMNICON. This machine or system automatically scans, selects and counts tumor colonies in the agarose culture within the petri dishes and uses optical and computer technology to obtain a faster and more accurate counting of the cell colonies. The machine has been used in basic research to study the effects of growth factors, carcinogens, promoters, growth inhibitory factors and differentiation inducers on single cells and on cell colonies.

In an effort to increase cloning efficiency and reduce perassay costs, a capillary cloning procedure has been developed and used as an alternative to the petri dish counting procedure. The cells are inserted into the capillary tubes and cell colonies are grown within the agarose culture. The cell colonies are counted manually by a person viewing the contents of each capillary tube through a microscope. Several years ago, a prototype automated data collection and analysis system was developed by Triton Biosciences Inc., a subsidiary of Shell Oil Company, for use with the capillary tube cloning technique. The prototype units were introduced under the trademark CELLSCAN and included an automated X-Y stage microscope, a rack for holding a set of capillary tubes each having a square cross-section, a DC-powered light source and a light detector and amplifier. All of these components were interfaced with a computer through a microprocessor. The light source was located directly above the object lens of the microscope on the vertical optical axis of the lens, and each capillary tube was moved longitudinally and horizontally through the optical axis for scanning the contents of each tube. A plate with a narrow slit was positioned between the downwardly directed light and the capillary tube under the light to restrict the illumination field. When a capillary tube was moved across the light directed through the slit, some data was collected with respect to the number and size of the cell colonies and the axial locations of the colonies within each capillary tube.

The square capillary tubes were selected to improve illumination of the cell colonies within the tubes since a conventional cylindrical capillary tube resulted in reflecting a high percentage of the light and poor illumination of the cell colonies. It was also determined that the use of the square capillary tubes and the illumination system used on the CELLSCAN unit resulted in a low signal-to-noise ratio from the optical detector. As a result, the accuracy and repeatability of the CELLSCAN system was not satisfactory, and further development of the system was discontinued in 1985 by Triton Biosciences Inc. In addition, since the square capillary tubes were made by fusing two L-shaped strips together, the tubes were expensive to manufacture, and the costs of the disposable tubes significantly increased the costs for each investigation.

SUMMARY OF THE INVENTION

The present invention is directed to an improved automated capillary scanning system and a method of scanning and counting the cells and cell colonies within the capillary tubes. The system and method are especially suited for basic and clinical investigations in a variety of fields including oncology, hematology, cell biology, virology and immunology. The apparatus of the invention provides for automatically scanning and selectively detecting the contents of a series of capillary tubes along the length of each tube and for obtaining a high signal-to-noise ratio from the optical detector. The apparatus of the invention further provides for an increased depth of field detection across the internal diameter of each capillary tube in order to provide for more complete and accurate analyzing of the tube contents.

In accordance with a preferred embodiment of the invention, the above-mentioned features and advantages are generally provided by a system which includes an automated microscope having an object lens with a vertical axis, an optical detector and a motor driven X-Y translation stage. A series of cylindrical glass capillary tubes are supported in the parallel spaced relation by a frame-like holder which is open at opposite ends to expose the opposite ends of each capillary tube. The holder and capillary tubes are precisely located on the translation stage, and the motors are controlled for selectively locating the horizontal axis of each tube at a position where it intersects the object lens axis and then moves each selected tube axially across the object lens axis.

The contents of each capillary tube are illuminated by a red precision light beam which is directed axially through each capillary tube when it intersects the object lens axis of the microscope. The light beam is generated by a helium-neon laser and is reflected by a set of mirrors some of which are adjustable to align the laser beam precisely with the object lens axis and the longitudinal axis of each capillary tube intersecting the object lens axis. The contents of the capillary tubes are scanned in sequence along the length of each tube by operation of the stage motors with a special program within a personal computer. The computer records and processes the detected optical signals corresponding precisely to the amount of light reflected by the cells and/or cell colonies within each capillary tube and further records the axial location of each cell and/or cell colony.

Other features and advantages of the invention will be apparent from the following description, the accompanying drawings and the appended claims.

BRIEF DESCRIPTION OF THE DRAWINGS

FIG. 3 is a greatly enlarged fragmentary section taken generally on the line 3—3 of FIG. 2 and showing the support of a typical capillary tube and its contents;

FIG. 4 is a fragmentary exploded view of the capillary tube holder and a portion of the optical stage; and FIG. 5 is an enlarged fragmentary section through the corner portions of two capillary tube holders arranged in stacked and nested relation.

DESCRIPTION OF THE PREFERRED EMBODIMENT

Figure 1:
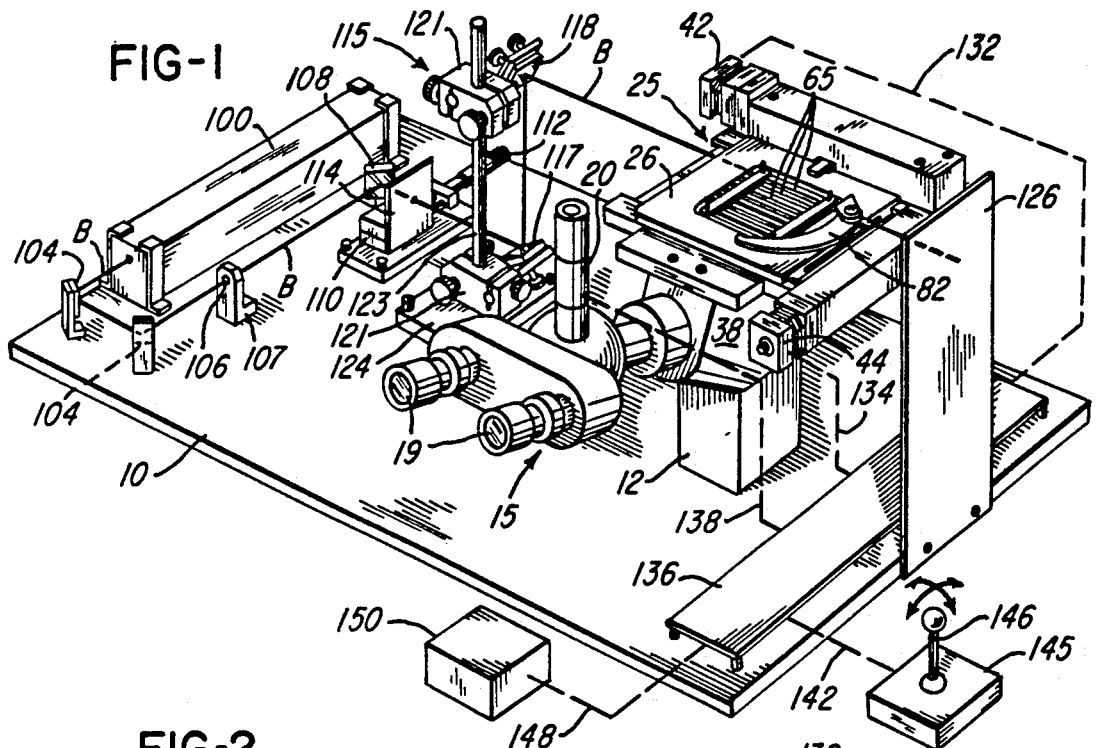
FIG. 1 is a perspective view of an automated capillary scanning system constructed in accordance with the invention.

Referring to FIG. 1, a rectangular base plate 10 is constructed of a heavy gauge aluminum and supports a block-like base portion 12 of an automated microscope 15. The microscope includes three selectable object lenses 17 (not all shown) having a vertical optical axis A, a pair of viewing lenses 19 and an electronic optical sensor or detector 20. One detector which has provided satisfactory results incorporates a photo-multiplier tube and is manufactured by Hamamatsu and sold as the Model 931A. The microscope 15 also includes an automated X-Y stage 25 formed by a rectangular frame-like top plate 26 supported for linear movement along an "X" axis 28 (FIG. 2) by a frame-like intermediate slide plate 32. The plate 32 is supported for linear movement on a "Y" axis 34 by a base plate 36 secured to the housing 38 of the microscope. A reversible electric motor 42 (FIG. 2) moves the plate 26 along the "X" axis 28, and a reversible electric motor 44 moves the plate 26 and the intermediate plate 32 along the "Y" axis 34. One type of microscope 15 which has provided satisfactory results is sold under the trademark OLYMPUS, and the stage is sold under the trademark SEMPREX. However, other brands of automated microscopes fitted with optical detectors and amplifiers and motor driven X-Y stages may be used.

Figure 2:
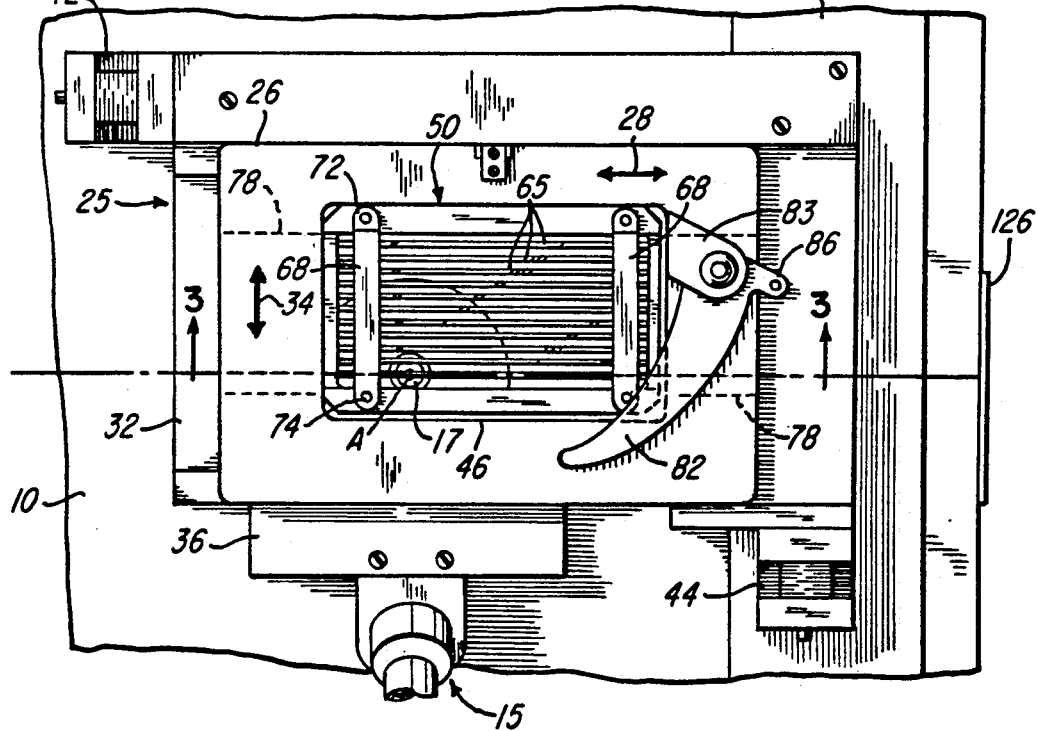
FIG. 2 is a fragmentary plan view of the motor driven translation stage and the holder of capillary tubes as used on the apparatus shown in FIG. 1.

Referring to FIGS. 2-4, the top plate 26 of the microscope stage 25 defines a rectangular opening 46, and a similar opening is formed within the slide plate 32. A circular opening 48 is formed within the base plate 36 of the stage 25 and is concentric with the object lens 17. A rigid frame-like rectangular tray or holder 50 is supported within the opening 46 by a shoulder or surface 53 projecting inwardly at the bottom of the opening 46. Preferably, the holder 50 is constructed of aluminum which is heat treated to prevent warpage and includes parallel spaced side frame members 54 integrally connected by thinner cross members 56 and a pair of rails 58 each having longitudinally spaced and precisionally formed recesses 59.

As shown in FIG. 4, a series or plurality of elongated glass capillary tubes 65 are supported by the parallel spaced rails 58 within the recesses 59, and the opposite ends of each tube 65 are spaced slightly above the corresponding cross members 56, as shown in FIG. 3. The capillary tubes 65 are retained within the corresponding recesses 59 by a pair of hold-down or clamping strips or members 68. Each clamping member 68 has a pair of holes 71 within its opposite end portions 72 for receiving a corresponding set of vertical pins 74 projecting upwardly from the side members 54 of the holder 50.

A strip 76 of resilient foam-like material is adhesively attached to the bottom surface of each clamping member 68 for contacting the capillary tubes 65 and for retaining the tubes within the corresponding recesses 59. Each of the members 68 is cut from a thin sheet of spring metal, and the end portions 72 of each member 68 are inclined upwardly for releasably gripping the corresponding pin 74 in a locking cant position. However, other means may be used for securing the hold-down members 68 to the pins 74. As shown in FIG. 5, a cylindrical cavity 77 is formed within the bottom of each corner portion of the holder 50 so that a plurality of the holders 50 may be stacked in interlocking or nesting relation.

As shown in FIGS. 3 and 4, the top frame plate 26 of the automated stage 25 has a pair of opposing slots 78 which align with the capillary tubes 65 when the holder 50 is positioned within the opening 46 on the surface 53 of the plate 26. The rectangular capillary tube holder 50 is biased or urged towards one side and one end of the slightly larger rectangular opening 46 by a pivotal finger 82 (FIG. 2). A pivot pin 83 supports the finger 82, and a torsion spring (not shown) urges the finger against one of the corner pins 74 so that the holder 50 and the parallel spaced capillary tubes 65 are precisely located relative to the top plate 26 of the optical stage 25. When it is desired to remove a set of capillary tubes 65 and their supporting holder 50 from the opening 46, the finger 82 is retracted by rotating the projection 86 counterclockwise (FIG. 2), and then lifting the holder 50 from the supporting surface 53.

A glass capillary tube 65 is shown in FIG. 3 with contents C filling only a center portion of the tube and having a miniscus M on each end. For example, a typical capillary tube 65 has an inner diameter of about 0.2 mm. and would contain 30 to 50 microliters of a tissue culture including a medium and an agarose and inserted into one end of the capillary tube 65 by an Eppendorf pipette. The combined agarose and medium changes from a liquid state to a gel state at a temperature under 42° C. Thus after the medium and agarose are inserted into the capillary tube in a liquid form at a temperature slightly above 42° C., the agarose is quickly cooled to form a clear or translucent gel which is maintained during the cloning and investigation of the cells suspended within the agarose gel. Preferably, the holder 50 is constructed to support a set of eighteen capillary tubes 65, although FIGS. 2 and 4 illustrate a lesser number for purpose of simplification.

Referring again to FIG. 1, a two milliwatt Helium-Neon laser 100 is rigidly mounted on one end portion of the base plate 10 and generates a pure red, polarized, collimated light beam B. One laser which has provided satisfactory results is manufactured by C J Laser Corporation and sold as the Model HNL-1020 C5. The light beam B is reflected by two folding mirrors 104 which are secured to the base plate 10 at 45° angles to the beam path. The beam B is either focused by an adjustment within the laser 100 or directed through an aperture 106 within a block 107 for limiting the diameter of the beam B to approximately the same as the inside diameter of a capillary tube 65, as shown in FIG. 3. This precision beam B is then reflected by an adjustable or gimbaled mirror 108 supported by a precision linear translation stage 110 having a micrometer adjustment knob 112. From the mirror 108, the beam B is directed through an alignment hole within a vertical plate 114 to a beam ladder 115. The beam ladder 115 includes two gimbaled or adjustable mirrors 117 and 118 which are supported by clamping blocks 121 adjustably mounted on a vertical post 123 projecting upwardly from a mounting plate 124 rigidly secured to the base plate 10.

The beam ladder 115 provides for elevating the light beam B to the level of the stage 25 and for directing the beam axially through each glass capillary tube 65 after it is located with its horizontal axis intersecting the vertical optical axis A of the object lens 17, as shown in FIG. 2. This precision path of the beam B is produced by adjusting the mirrors 108, 117 and 118. The mirror 108 provides for shifting the light beam B horizontally in response to adjusting the micrometer knob 112 for precisely locating the horizontal light beam B at a position where it intersects the vertical optical axis A of the object lens 17. The lower mirror 117 of the beam ladder 115 is adjusted for precisely positioning the light beam B with respect to the entrance or left end (FIG. 3) of the capillary tube 65, and the upper mirror 118 is adjusted for precisely positioning the beam B relative to the exit or right end of the capillary tube. Thus the mirrors 117 and 118 are used to position the light beam B in precise axial alignment with the capillary tube 65 intersecting the optical axis A of the object lens 17.

As shown in FIGS. 1-3, a beam blocking plate 126 is mounted on the right edge of the base plate 10 and is preferably painted black along with other components of the system so that a red circular dot appears on the inner surface of the plate 126 when an empty capillary tube is moved into axial alignment with the light beam B. As mentioned above, the laser 100 preferably generates a pure red light beam, and the optical sensor or detector 20 is selected so that it is particularly sensitive to the red light of the beam B. This contributes to obtaining a high signal-to-noise ratio.

As diagramatically illustrated in FIG. 1, flexible electrical conductors 132 and 134 connect the motors 42 and 44 of the optical stage 25 to a control circuit (not shown) located under an elongated panel 136 spaced above the base plate 10. Additional electrical conductors 138 connect the optical sensor or detector 20 to the control circuit, and flexible conductors 142 connect the control circuit to a manual control box 145 having a tiltable joy stick 146 for manually operating the stage motors 42 and 44 to move the holder 50. The control circuit incorporates a microprocessor (not shown), and a flexible cable 148 connects the control circuit to a personal computer 150 which receives and stores the electrical signals from the detector 20 and controls the operation of the stage motors 42 and 46 according to a special program prepared for the computer.

In operation of the apparatus described above, the center portions of the capillary tubes 65 receive the clear or translucent contents C as mentioned above in connection with FIG. 3. For example, three of the capillary tubes might receive a control culture of human tumor cells suspended within the medium and agarose gel. The remaining fifteen capillary tubes 65 may include the identical culture as the first three tubes but with the addition of five different chemotherapy drugs with three tubes assigned to each drug. The program for the computer 150 controls the stage motors 42 and 46 so that the series of capillary tubes 65 are scanned longitudinally and in sequence from the left miniscus M to the right miniscus M. Prior to scanning the contents of the capillary tubes, the laser 100 is energized so that the collimated light beam B illuminates the entire contents C of each capillary tube after the tube is moved by the stage 25 so that its longitudinal axis intersects the optical axis of the lens 17.

From the drawings and the above description, it is apparent that a capillary scanning system constructed in accordance with the invention and its method of use, provide desirable features and advantages. For example, one important feature is provided by the illumination of the contents C of each capillary tube 65 by use of the axially directed precision or collimated light beam B. That is, substantially all of the light emitted by the laser 107 is confined within the capillary tube by total internal reflection and only the light which illuminates a particle such as a cell or cell colony is scattered outwardly through the wall of the capillary tube and to the detector 20. The intensity of the scattered light corresponds precisely with the size, shape and orientation of the cell or cell colony, and all of the cells or cell colonies within the capillary tube are illuminated uniformally by the light beam B.

As another advantage, the internal illumination of the contents C of each capillary tube 65 from the end of the tube provides for obtaining a high signal-to-noise ratio from the detector 20 so that maximum sensitivity and accuracy are obtained. Furthermore, by focusing the microscope on the glass wall of the capillary tube, the depth of field detection of scatter light is increased to the entire inside diameter of the capillary tube so that all of the cells or cell colonies within the contents C are precisely detected. In addition, after the gel suspending the cells or cell colonies within each capillary tube 65 is solidified, the axial location of each cell or cell colony is fixed. Thus when the contents of each capillary tube is scanned in accordance with the invention, the computer 150 not only records the intensity of the light reflected by each cell or cell colony to the detector 20, but also records the axial location of each cell and/or cell colony within the tube. As a result, the contents of the capillary tubes within each holder 50 may be scanned after predetermined time periods during which the tubes and contents are placed in an incubator, so that the progressive effect on specific cells and cell colonies by the different drugs may be determined.

As mentioned above, the apparatus of the invention has many uses, especially in the fields of cell cloning, drug sensitivity testing and basic biological studies. Preferably, the computer 150 is programmed to take several thousand readings along the axial length of the contents C within each capillary tube and to record the reflected light intensity at each reading. It is preferred that the computer 150 be compatible with an IBM/PC XT or AT computer and be provided with a printer for documenting the recorded results obtained from the axial scanning of each capillary tube.

Further advantages are provided by the capillary tube holder 50 which supports the tubes so that opposite ends of each tube are exposed, and especially to the light beam B extending through the slots 78 and over the cross members 56 of the holder 50. The exposed ends of the tubes 65 within the holder 50 also provide for connecting each tube to a perfusion pump for subjecting the contents C of each tube to a special fluid which penetrates the contents C by osmosis so that the effect of the fluid on the contents over a period of time may be determined. As also mentioned above, the cylindrical glass capillary tubes 65 are commonly used in laboratory experiments and are commerically available at minimal costs.

While the method and form of apparatus herein described constitute a preferred embodiment of the invention, it is to be understood that the invention is not limited to the precise method and form of apparatus described, and that changes may be made therein without departing from the scope and spirit of the invention as defined in the appended claims.

The invention having been described, the following is claimed:

1. Apparatus for scanning and detecting the contents of an elongated capillary chamber having an axis and defined by light transmitting means, comprising an optical sensor having a predetermined optical axis, means for supporting said light transmitting means to position said capillary chamber with its axis substantially intersecting said optical axis, means for producing relative movement between said optical sensor and said supporting means to move said capillary chamber axially across said optical axis, means for generating a precision light beam, means for directing the light beam towards said capillary chamber at a substantial angle relative to a plane perpendicular to the axis of said chamber for illuminating the contents of said capillary chamber without producing significant reflection and refraction of light by said light transmitting means to said optical sensor, and said optical sensor including means for detecting differences in the light reflected by the illuminated contents of said capillary chamber along the length of said chamber.

2. Apparatus as defined in claim 1 wherein said light transmitting means define a plurality of said capillary chambers in parallel spaced relation, said means for producing relative movement including an optical X-Y stage having motor driven means for moving said chambers in each of two perpendicular directions for locating each said capillary chamber at said optical axis with the light beam disposed at said angle relative to said plane.

3. Apparatus as defined in claim 1 wherein said angle is 90 degrees and the light beam is directed axially through said capillary chamber when the axis of said chamber intersects said optical axis.

4. Apparatus as defined in claim 3 wherein said means for generating a precision light beam comprise a laser unit, and means for adjusting said directing means for changing the position of said light beam to obtain precise axial alignment with said capillary chamber.

5. Apparatus as defined in claim 3 wherein said light transmitting means define a plurality of said capillary chambers in parallel spaced relation, said supporting means comprise a removable holder for said light transmitting means, and said chambers have corresponding open ends for directing the light beam axially into each said chamber.

6. Apparatus as defined in claim 5 wherein said optical sensor comprises a microscope including an electronic optical detector, said microscope further including a motor driven X-Y stage supporting said holder, and said holder defines an opening for directing the light beam axially into each of said capillary chambers.

7. Apparatus as defined in claim 5 wherein said holder includes means for receiving and locating another said holder in stacked and interconnected relation.

8. Apparatus for scanning and detecting the contents of an elongated capillary chamber having an axis and defined by light transmitting means, comprising an optical sensor having a predetermined optical axis, means for supporting said light transmitting means to position said capillary chamber with its longitudinal axis substantially intersecting said optical axis, means for producing relative movement between said optical sensor and said supporting means to move said capillary chamber axially relative to said optical axis for scanning the contents of said chamber, means for generating a precision light beam, means of directing the light beam axially through said capillary chamber for illuminating the contents of said capillary chamber, and said optical sensor including means for detecting differences in the light reflected by the illuminated contents of said capillary chamber along the length of said chamber.

9. Apparatus as defined in claim 8 wherein said supporting means comprise a holder, said light transmitting means define a plurality of said capillary chambers in parallel spaced relation, said means for producing relative movement including an X-Y translation stage having motor drive means for moving said holder in each of two perpendicular directions for locating each said capillary chamber in axial alignment with the light beam an for moving each said capillary chamber axially across said optical axis.

10. Apparatus as defined in claim 8 wherein said means for generating a precision light beam comprise a laser unit, and means for adjusting said directing means for changing the position of said light beam to obtain precise axial alignment with said capillary chamber.

11. Apparatus as defined in claim 8 wherein said capillary chamber is generally cylindrical, and the light beam has a diameter generally the same as the diameter of said chamber.

12. Apparatus as defined in claim 8 wherein said means for directing the light beam comprise a set of mirrors, and means for adjusting said mirrors.

13. Apparatus as defined in claim 8 wherein said supporting means comprise a frame-like holder, said light transmitting means define a plurality of said capillary chambers in parallel spaced relation, and said chambers have common open ends for directing the light beam axially into each said chamber.

14. Apparatus as defined in claim 13 wherein said optical sensor comprises a microscope including an electronic optical detector, said microscope further including a motor driven X-Y stage, said stage supports said holder, and said holder defines an opening for receiving the light beam directed to each said capillary chamber.

15. Apparatus as defined in claim 13 wherein said holder includes means for receiving and locating another said holder in stacked and interconnected relation.

16. Apparatus for scanning and detecting the contents of a series of elongated capillary chambers each having an axis and defined by light transmitting means, comprising an optical sensor including an object lens with a predetermined optical axis, a holder for supporting said light transmitting means with said capillary chambers in parallel spaced relation, an X-Y translation stage having motor drive means supporting said holder for movement in each of two perpendicular directions for locating each said capillary chamber with its longitudinal axis substantially intersecting said optical axis and for moving each said capillary chamber axially across said optical axis, a laser unit for generating a precision light beam, means for directing the light beam axially through each said capillary chamber when said chamber is positioned by said holder to intersect said optical axis for illuminating the contents of said capillary chamber, and said optical detector including means for detecting differences in the illuminated contents of each said capillary chamber along the length of said chamber.

17. Apparatus as defined in claim 16 wherein said means for directing the light beam comprise a set of adjustable mirrors.

18. Apparatus as defined in claim 16 wherein the light beam has a diameter generally the same as the inside diameter of said capillary chamber.

19. Apparatus as defined in claim 16 and including means for interconnecting a plurality of said holders in stacked relation.

20. Apparatus as defined in claim 16 wherein said object lens of said optical sensor has a focal point substantially on said light transmitting means defining each said capillary chamber.

21. A method of scanning and detecting the contents of an elongated capillary chamber having an axis and defined by light transmitting means, comprising the steps of supporting the light transmitting means in relation to an electronic optical detector having an optical axis, positioning the chamber with its axis intersecting the optical axis, directing a beam of light axially into the chamber to illuminate the contents, moving the chamber axially relative to the optical axis for scanning the chamber contents, and detecting the light reflected outwardly through the light transmitting means by particles within the contents along the length of the chamber.

22. A method of scanning and detecting the contents of a series of elongated capillary chambers defined by light transmitting means, comprising the steps of locating the chambers in parallel spaced relation and with corresponding ends of the chambers being exposed, supporting the light transmitting means with a motor driven X-Y stage in relation to an electronic optical detector having an optical axis, moving the light transmitting means for successively positioning the chambers where the longitudinal axis of each chamber intersects the optical axis, directing a beam of light axially into each chamber while intersecting the optical axis to illuminate the contents of the chamber, moving the light transmitting means to move each chamber axially relative to the optical axis for scanning the contents of each chamber, and detecting the light reflected outwardly through the light transmitting means by particles within the contents along the length of each chamber.

23. A method as defined in claim 22 wherein the beam of light is red, and the detecting is performed by a detector sensitive to red.

* * * * *